United States Patent [19]
Jones

[11] 3,989,478
[45] Nov. 2, 1976

[54] PRODUCING GASEOUS FUELS OF HIGH CALORIFIC VALUE

[75] Inventor: James Kevin Jones, Stalybridge, England

[73] Assignee: Petrocarbon Developments Limited, Manchester, England

[22] Filed: Mar. 24, 1976

[21] Appl. No.: 669,886

Related U.S. Application Data

[63] Continuation-in-part of Ser. No. 447,887, March 4, 1974, abandoned.

[30] Foreign Application Priority Data

Sept. 27, 1973  United Kingdom............... 45364/73

[52] U.S. Cl. ............................. 48/196 R; 48/197 R; 55/23; 55/80; 60/39.12; 62/11; 62/36; 166/267
[51] Int. Cl.² ........................................... C10J 1/00
[58] Field of Search........ 48/89, 128, 196 R, 197 R, 48/212; 55/23, 29, 30, 80; 60/39.12, 39.18 C; 62/9, 11, 17, 18, 23, 24, 27, 28, 31, 32, 34, 36, 38, 41, 42, 44; 166/267

[56] References Cited
UNITED STATES PATENTS

| | | | |
|---|---|---|---|
| 2,598,785 | 6/1952 | Groebe et al............................ | 55/23 |
| 3,213,631 | 10/1965 | Kniel....................................... | 62/11 |
| 3,494,751 | 2/1970 | Streich............................... | 48/196 R |

OTHER PUBLICATIONS

Gas Engineers Handbook, "Liquified Natural Gas and Nonconventional Natural Gas Storage," p. 10127.

Primary Examiner—Robert L. Lindsay, Jr.
Assistant Examiner—George C. Yeung
Attorney, Agent, or Firm—Burgess, Ryan and Wayne

[57] ABSTRACT

Process for upgrading an air-contaminated methane composition such as is found near coal measures comprises condensing this gas, and thereafter fractionating it to yield a first product having a methane content higher than that of the initial composition and a calorific value commensurate with that of natural gas, and a second product having a methane content below that of the initial composition but above the highest limit of the flammability range for methane-air mixtures under the conditions of temperature and pressure prevailing in the process.

17 Claims, 1 Drawing Figure

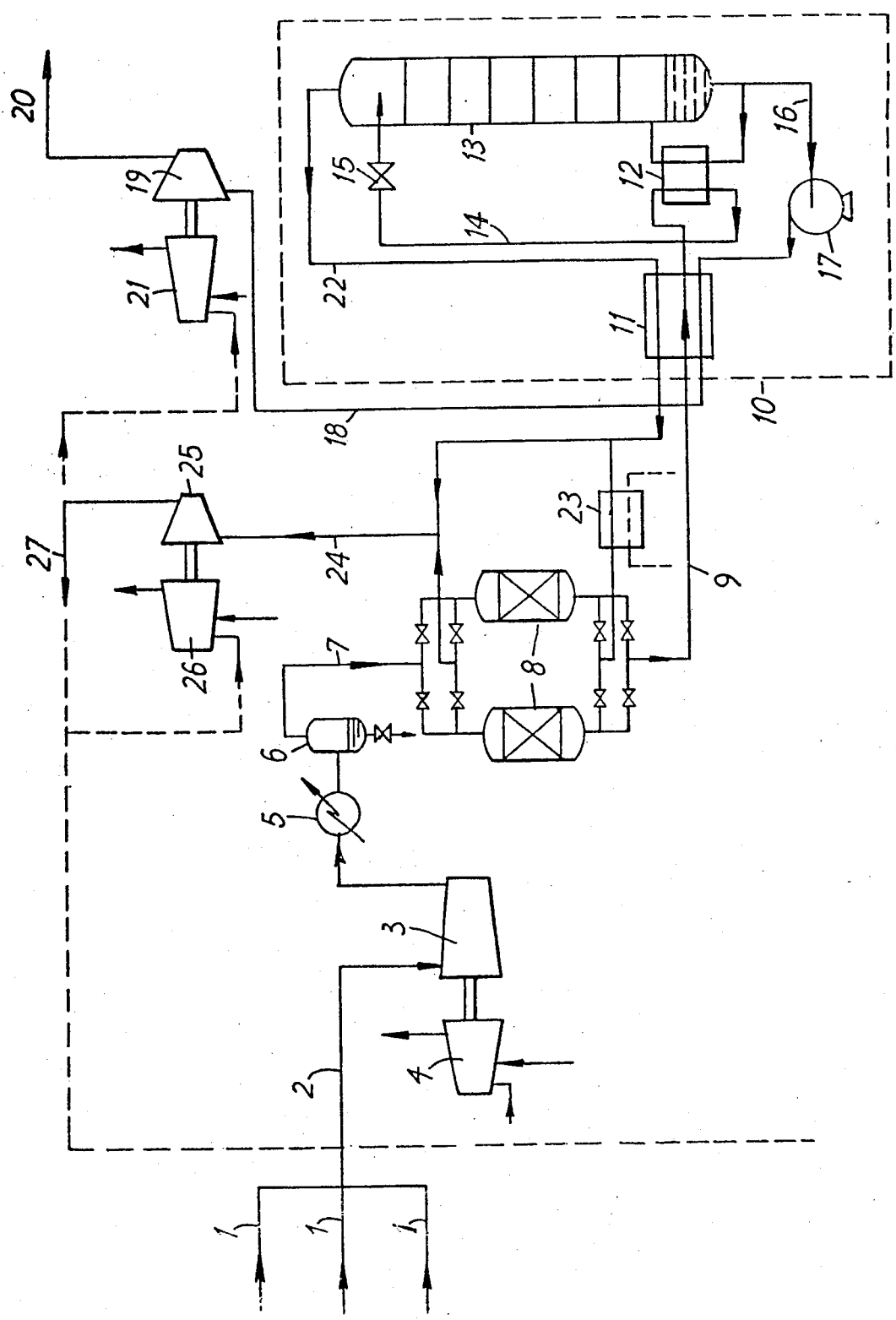

PRODUCING GASEOUS FUELS OF HIGH CALORIFIC VALUE

This is a continuation-in-part of Ser. No. 447,887, filed Mar. 4, 1974, now abandoned.

This invention relates to the production of a gaseous fuel of high calorific value, commensurate with that of natural gas which has a calorific value of about 1000 BTU/cu ft, from methane contaminated with minor but significant quantities of air.

In the vicinity of some coal measures, a gas is found which consists essentially of methane contaminated with minor but significant quantities of air, e.g. as much as 20% to 30%. The methane may result from the decomposition of the coal or other carboniferous matter. Alternatively, it may percolate into the coal measure from a pocket or well of natural gas located in the neighbourhood of the coal measure. The air with which the methane is contaminated may be air used to ventilate those parts of the coal measure which are being mined. Whatever the source of the methane or the air, however, the disposal of the resultant mixture has created problems because of the danger of explosion. On the other hand the present practice of venting the mixture to atmosphere results in the waste of potentially valuable fuel.

According to the present invention, there is provided a process of upgrading such an air-contaminated methane gas composition. The process comprises condensing this gas, and thereafter fractionating it to yield a first product having a methane content higher than that of the initial composition and a calorific value commensurate with that of natural gas, and a second product having a methane content below that of the initial composition but above the highest limit of the flammability range for methane-air mixtures under the conditions of temperature and pressure prevailing in the process.

Apparatus is also provided, comprising in combination, first, second and third compression means each having a gas inlet and a gas outlet; gas-fuelled prime mover means for driving said first, second and third compression means; indirect countercurrent heat exchange means; expansion valve means; a fractionating column having an inlet, a liquid outlet below said inlet and a gas outlet above said inlet; a pump having an inlet and outlet; means for feeding said composition to the inlet of said first compression means; means for passing compressed composition from the outlet of said first compression means through said indirect countercurrent heat exchange means and then through said expansion valve means where it is expanded to a lower pressure and thence to the inlet of said fractionating column; means for recovering a liquid product from the liquid outlet of said fractionating column and recycling a first portion of said product through said heat exchange means in indirect countercurrent heat exchange with said compressed composition and back to the fractionating column; means for passing a second portion of the liquid product to the inlet of said pump; means for passing the liquid product from the outlet of said pump through said heat exchange means in indirect countercurrent heat exchange with said compressed composition and thence to the inlet of said second compression means; means for recovering a compressed fuel gas from the outlet of said second compression means; means for recovering a gaseous product from the gas outlet of said fractionating column, passing it through said heat exchange means in indirect countercurrent heat exchange with said compressed composition and thence to the inlet of said third compression means; and means for recovering a compressed lean fuel gas from the outlet of said third compression means and for feeding said gas as fuel to said prime mover means.

A preferred method of carrying out the invention comprises compressing the air-contaminated methane gas composition to elevated pressure, cooling the compressed gas to condense it, expanding the condensate to fractionation pressure and using the sensible and latent cold in the product streams from the fractionation in said cooling of the compressed gas by effecting indirect counter-current heat exchange between on the one hand said compressed gas and on the other hand said product streams. Where, in this preferred method, it is desired to compress the first product stream to a pressure above the fractionation pressure; e.g. to raise it to a pressure suitable for its subsequent utilisation as a fuel gas stream, this is preferably achieved, so far as is possible, prior to effecting heat exchange between it and the compressed composition, since prior to said heat exchange the first product stream is substantially liquid and the power requirements for pumping it when in the liquid state are much smaller than when in the gaseous state. However, the degree to which the pressure of the liquid stream can be raised will be limited by the requirement that it evaporates in said heat exchange step. Thus, any further pressurisation that is required should be effected on the first product stream after the heat exchange step when it will be in substantially gaseous form.

While the process is equally applicable to other air-methane mixtures containing minor but significant proportion of air in them, irrespective of their source or the manner of their formation, it is particularly suitable for the treatment of air-contaminated methane gases found in the vicinity of coal measures.

Where a plurality of streams of air-contaminated methane gas are recoverable from geographical locations which are close to one another, e.g. from a plurality of spaced locations above a coal measure or group of geographically related coal measures, they may be combined for treatment in accordance with the method of the invention. In general, such gas streams are at about atmospheric pressure or slightly less than atmospheric pressure and they may suitably be brought together for the treatment by means of a vacuum pump located in the vicinity of the fractionation plant. Advantageously this pump may comprise a compressor designed to operate with the inlet side under vacuum whereby it may also compress the combined stream to the desired pressure for subsequent condensation. By this means, gas streams may be collected from a distance of several miles away.

In the process of the invention, as indicated above, it is preferred to compress the feed gas mixture prior to condensing it. It is to be understood, however, that the maximum pressure to which the feed is compressed should be safely below that pressure at which the feed mixture becomes spontaneously explosive. The lower and upper flammability limits for methane-air gas mixtures at ambient temperature and atmospheric pressure are at about 5% and 14% methane respectively. However, the upper limit increases with rising pressure, reaching about 25% at 50 atmospheres and 35% at 100 atmospheres. In general, however, pressures of less than 50 atmospheres are found adequate for the compression of the feed and it will be seen that for feed mixtures containing 30% air, the rest being substantially methane, such pressures fall well below that at which there may be a chance of explosion.

The upper limit of methane concentration for flammability also increases with rising temperature but the change is insignificant below 600° C and can therefore be ignored for the purposes of the present invention.

For the first product to be readily saleable as a fuel gas, it should have a calorific value of at least 950 BTU/cu.ft. This is equivalent to a methane content of about 94%. Thus, the fractionation should be conducted to produce a bottom fraction containing at least 94% and preferably at least 96% methane.

The second product must have a methane content such that it is above the highest limit of the flammability range of methane-air mixtures under the conditions of temperature and pressure prevailing in the fractionation column. The value for the upper flammability limit is given above and is its dependence on temperature and pressure. In general, the fractionation process will be operated well below ambient temperature and at a slightly superatmospheric pressure, and it will thus be recognized that methane concentrations in the second product of about 20% or above will give a satisfactory margin of safety under such conditions and that this product will also be safe to handle at ambient temperatures and moderately elevated pressures.

The upper limit of the methane concentration for flammability also increases with oxygen-enrichment of the air in the mixture, the upper limit reaching 60% methane for methane-pure oxygen mixtures. In the process of the invention, however, it will be appreciated that as nitrogen has a lower boiling point than both oxygen and methane, the section of the fractionation column in which any oxygen enrichment will occur will also be that in which the methane content is higher than that of the feed mixture so that the danger of reaching the flammability limit resulting from oxygen enrichment can be avoided. In any event, it is not necessary to pursue the fractionation to a point at which extensive oxygen-enrichment of the air component of the air-methane mixture will occur.

The rates of production of the first and second products will be set by the methane content of the air-contaminated methane stream to be treated and the desired composition of the first and second products.

The second product of the fractionation has value as a fuel since it can be combusted with additional air. Thus, at least a part of the energy requirements of the process of the invention can be supplied by combustion of a fuel gas provided by this second product, for instance by providing one or more gas engines or gas turbines adapted to be fuelled by such gas to drive pumps and/or compressors required by the process.

In general, the greatest power requirements of the process are for compressing the air-contaminated methane prior to condensing it, and, where desired, for compressing the first and second products of the fractionation to elevated pressures suitable for their subsequent utilisation as fuel gas streams.

Where the composition of the feed allows, it is preferred to arrange the fractionation to produce a second product having a fuel value and rate of production such that its combustion can provide at least the total energy requirements for compressing the air-contaminated methane prior to condensing it, and, if required, compressing both the first product and second product to an elevated pressure suitable for their subsequent utilisation as fuel gas streams, as well as a first product having a calorific value of 950 to 1000 BTU/cu.ft. in commercially adequate quantities. With most contemplated feed streams such conditions can be achieved without difficulty.

If desired, the fractionation can be arranged to produce a second product of such fuel value and in such quantities as to satisfy all the energy requirements of the process while still producing a first product of satisfactory quality at a commercially acceptable rate.

There can thus be provided a self-contained plant for producing a saleable fuel gas from air-contaminated methane gas, which plant has no need of any outside service for its main energy source or at all. However, in certain circumstances, it may prove more practicable to utilise available services; e.g. electricity to drive small pumps and/or water for cooling.

It will be generally desirable to remove from the initial mixture prior to condensing it any contaminants which would freeze at the temperatures employed for the fractionation. This may be achieved in known manner by passing the initial mixture through adsorber means comprising one or more beds of one or more suitable types of adsorbent, each adsorbent being selected for its ability to adsorb from the mixture one or more such contaminants, of which the most usual will be moisture.

Suitably, the adsorber means may comprise in known manner at least two beds of adsorbent arranged for cyclic operation such that in each period of the cycle the initial mixture is being passed through at least one of the beds and at least another of the beds is being regenerated ready for re-use in a subsequent period of the cycle.

In general, the regeneration is effected by passing through the bed a regeneration gas which will purge the bed of the contaminant or contaminants which the bed has adsorbed in a previous period of the cycle. Regeneration is generally assisted by lowering the pressure and/or raising the temperature of the adsorbent bed.

In the process of the present invention, this regeneration gas may conveniently be provided by a portion of the first and/or second products of the fractionation.

Where the contaminants are such that they can be tolerated in the first or second product the regeneration gas leaving the adsorber and containing the contaminant or contaminants desorbed from the adsorbent bed may be recombined with the remainder of the first or second product, as appropriate, for subsequent use as a fuel gas. This method of regeneration is particularly applicable to the case where the contaminant is moisture.

Where it is found desirable to heat the regeneration gas prior to passage through the adsorber means in order to promote regeneration of the adsorbent as described above and thereby reduce the quantity of gas required to desorb a given quantity of contaminant, some or all of the heat may advantageously be provided directly or indirectly by the combustion of a fuel gas provided by the second product of the fractionation. Where one or more gas engines and/or gas turbines are provided as prime movers e.g. for one or more of the compressors required by the process, the hot exhaust gases from one or more of said engines or turbines may provide some or all of the required heat.

Where the initial mixture is freed of moisture by passage through a bed or beds of adsorbent, the vessels containing the adsorbent beds tend to be relatively large so that it is economically undesirable to subject these vessels to the temperature changes found desirable for effecting efficient regeneration. In such cases, it is usual to insulate the beds of adsorbent from the vessels. Insulation that is not sensitive to pressure changes tends to be expensive and therefore in order to avoid such expense it is desirable that the difference between the pressure of the gas being treated by the adsorbent and the pressure of the regeneration gas is as small as possible. To this end, it may be desirable to raise the pressure of the first or second product substantially above the pressure at which it is recovered from the fractionation prior to using it as a regenerating gas for the adsorbent. Thus, where the product gas to be used as the regenerating gas is also compressed to an elevated pressure for subsequent use as a fuel gas, it is advantageous to derive the regeneration gas from said compressed fuel gas.

This invention is now described in more detail with reference to its application to air-contaminated methane streams recovered from the vicinity of coal measures, and with the aid of the flow diagram in the accompanying DRAWING.

The air-contaminated methane streams recovered from coal measures normally issue at near atmospheric pressure from a number of ventilation shafts situated at some distance from one another. It is convenient to bring these streams together at a suitable location for upgrading in a central plant since the alternative of installing compression equipment with separate power sources at the various gas outlets would be expensive and cumbersome.

The gas streams from the available emission points are collected in the pipes 1 and combined at the central installation in the pipe 2 by means of a combined vacuum pump-compressor 3 which is driven by a gas-powered prime mover 4. The vacuum compressor may be of the centrifugal, rotary or reciprocating type according to the required throughput and the specific location and conditions, and the prime mover may be, for example, a gas engine or a gas turbine.

The gas leaves the vacuum pump compressor at a delivery pressure, e.g. of about 600 psig, which is chosen to be sufficiently high for all the refrigeration for the fractionation process to be supplied by subsequent expansion of the compressed gas. The compressed gas then passes through a cooler 5, in which most of the moisture contained in it condenses, and thence to a separator 6 in which the water is removed. The cooler may be water-cooled or alternatively air cooled in which case the need for a water supply to the plant is obviated. Where is it air-cooled, the air impeller may be driven by an electric motor or alternatively a gas-fuelled prime mover if, for example, no electricity supply is readily available.

Leaving the separator through pipe 7, the compressed gas passes to an adsorber means where it is directed through one of the two adsorber vessels 8 which alternate in use so that while one is adsorbing the other is being regenerated ready for re-use for adsorption. The adsorber vessel may be filled with activated carbon, activated alumina, molecular sieves or any other adsorbent material, or a combination of several suitable adsorbents, suitable for removing residual water vapour from the gas by adsorption. The adsorber vessels are switched over at regular intervals in known manner and the adsorbent in each vessel is regenerated after each adsorption period with a gas the composition of which is described later.

Leaving the adsorber means through pipe 9, the compressed gas enters the cooled section of the plant which may suitably be contained in an insulated cold box 10. Here it is cooled and completely condensed in the heat exchanger 11 by counter-current indirect heat exchange with evaporating liquid and gaseous fractionation products and then sub-cooled in the re-boiler 12 of the stripping column 13 by indirect counter-current heat exchange with a portion of the liquid fractionation product, this liquid product portion being evaporated by said heat exchange.

The sub-cooled liquid leaves the re-boiler through pipe 14 and is expanded to a low superatmospheric pressure, which may suitably be 5-10 psig, to partially vaporise it, and fed to the top of the stripping column 13. The conditions within the stripping column are controlled to produce a first product comprising a rich liquid methane fraction and a second product comprising a lean fuel gas containing sufficient methane to maintain it outside the flammability limits. It will thus be evident that the liquid and vapour mixtures passing through the stripping column will all remain outside the range of flammability of methane-air or methane-oxygen enriched air mixture.

Part of the methane rich liquid is recirculated back to the column 13 through reboiler 12 where it is evaporated by indirect counter-current heat exchange with the incoming condensed mixture which is simultaneously sub-cooled as described above. The remainder of the methane rich liquid fraction leaves the column through pipeline 16 and its pressure is raised in the pump 17 to the maximum level that is compatible with the thus-compressed liquid still evaporating in heat exchanger 11. This level will be around 300 psig. The ratio of the rates of flow of the methane-rich liquid to the pump 17 and to the reboiler 12 controls the conditions in and composition of the products from the fractionation column in known manner.

The stream from pump 17 is then evaporated and warmed in the heat exchanger 11 in indirect counter-current heat exchange with the incoming compressed mixture as described above, and passed by way of the pipe 18 out of the cold box and thence to the suction of a compressor 19 which it leaves through pipe 20 at a pressure suitable for distribution as a fuel gas stream.

The compressor 19 is driven by a gas-fuelled prime mover 21 and the type of compressor 19 and its associated power unit 21 may be chosen according to the specific conditions and requirements.

The lean fuel gas leaves the top of the stripping column 13 through the pipe 22, is warmed to near ambient temperature in the heat exchanger 11 by counter-current indirect heat exchange with the incoming compressed mixture and is subsequently fed through pipeline 24 to compressor 25 in which its pressure is raised to whatever value is required for feeding into the fuel line 27, e.g. about 350 psig.

The compressor 25 is driven by the gas powered prime mover 26 and again, the type of compressor and prime mover can be chosen to suit the particular circumstances.

To regenerate the adsorbent in the beds of the adsorbers 8, a part of the lean fuel gas stream leaving heat exchanger 11 is removed, warmed in heater 23 and passed through whichever of the adsorber beds requires regenerating. The regeneration gas recovered from the adsorbers is then returned in pipeline 24 for feeding to the compressor 25.

The heater 23 is preferably heated by burning fuel gas from the fuel line 27 but it may also be heated by exhaust gases from one or more of the prime movers 4, 21 and 26, or by any other suitable method.

If it is desired for the regeneration gas to be at a pressure nearer that of the compressed gas stream being treated by the adsorbers, the regeneration gas may alternatively be provided from the pipeline 27. In yet another alternative, the regeneration gas may be provided by the first product stream e.g. from pipeline 18 or, where it is desired to use a higher pressure, from pipeline 20.

The gas-powered prime movers 4, 21 and 26 are all advantageously adapted to be fuelled by the compressed lean fuel gas in fuel line 27, as shown. The pump 17 and any air impeller used for cooler 5 may each also be driven by a gas-powered prime mover adapted to be fuelled by compressed lean fuel gas from fuel line 27 but the power requirements of these pieces of equipment are relatively small and it may be more econonic to use small electric motors.

By means of the invention a methane rich product containing about 4% oxygen-nitrogen mixture, having a calorific value of 980 BTU/cu ft and delivered at 500 psia, and a lean gas containing 22% methane and which is produced in sufficient quantities to provide the total fuel requirements of the prime mover for the compressors, can be obtained from a gas mixture containing 21–31 mole % air, 68–78% methane and 1% ethane.

By using a vacuum pump-compressor to compress the mixture, the vacuum pump-compressor having a design suction inlet pressure of 10 psia and a delivery pressure of 600 psia, the gas mixture can be drawn from points several miles from the plant. The pressure of the stripping column 13 is 22 psia and the compressed mixture is cooled to about −100° C in heat exchanger 11 whereby it is condensed, and thereafter sub-cooled to about −150° C in heat exchanger 12. It is then expanded to 22 psig through expansion value 15 and fed to stripping column 13 for fractionation at this pressure. The fractionation is controlled to produce first product and second product in the ratio of about 64:36 by volume and the rich methane liquid leaving the bottom of the column is recompressed to 300 psia by pump 17 after which it returns through exchanger 11, where it is evaporated and warmed to near ambient temperature. It is then further compressed to 500 psia in the compressor 19 for subsequent onward transmission to the user. The lean gas leaving the top of the column 13, after passing through the heat exchanger 11 where it is warmed to near ambient temperature, is compressed to 350 psia in compressor 25. The heating value of this gas is sufficient to drive the prime movers 4, 21 and 26.

It will thus be seen that the completely self-contained and self-sufficient plant can be provided for the production of saleable fuel gas, having a calorific value commensurate with that of natural gas, from an air-contaminated methane gas composition.

The plant can be adapted without difficulty to produce a first product having a calorific value in the range of 950 to 1000 BTU/cu. ft.

The invention is now illustrated in non-limitative fashion by the following example.

EXAMPLE

Employing the equipment and process described above with reference to the drawing, a feed stream comprising 69% methane, 1% ethane and 30% air was collected and passes through pipeline 2 to compressor 3 where it was compressed to a pressure such that after passage through cooler 5, separator 6 and one of the adsorber vessels 8, it was fed through pipeline 9 to heat exchanger 11 at 600 psia. In heat exchanger 11, this stream was cooled by indirect counter-current heat exchange with streams, hereafter identified, in pipelines 18 and 22 from 300°K to 140.7°K. The cooled stream was then passed through fractionation column reboiler 12, where it was further cooled to 120°K, and then via pipeline 14 to expansion valve 15 where it was expanded to 22 psia and further cooled by this expansion to 110°K.

It was then fed into the fractionation column 13 near the top. The fractionation column was at 22 psia pressure and was operated so as to provide an overheat temperature of 101°K and a bottoms temperature of 115°K.

Under these conditions, a gaseous overhead product was obtained containing 22% methane and 78% air and a liquid bottoms product was obtained containing 94.5% methane, 1.5% ethane and 4.0% air.

Although for convenience the overhead and bottoms product are stated to contain 78% air and 4.0% air respectively, it will be understood that a certain amount of separation of the oxygen and nitrogen in the air will have occurred under the fractionation conditions so that the nitrogen-to-oxygen ratio in the overhead product will be somewhat greater than 4:1 while the ratio in the bottoms product will be somewhat less than 4:1. However, this difference has such a small effect on the enthalpies and the dew and bubble points of the overhead and bottom products that it can be ignored for all practical purposes. For example, even if the nitrogen-to-oxygen ratio is reduced to as low as 2:1 in the bottoms product, which is an extreme case, the bubble point of the bottoms product will be changed by less than 1°C.

The liquid bottoms product was recovered from the fractionation column in pipeline 16 and passed to the pump 17 where it was compressed to 300 psia and then passed in pipeline 18 through heat exchanger 11 where it was evaporated and warmed to 297°K in indirect counter-current heat exchange with the incoming feed. It was then passed to compressor 19 where it was further compressed for subsequent utilisation as a fuel gas. It had a fuel value of 978 BTU/cu.ft.

The overhead product from the fractionation column was recoovered in pipeline 22 and also passed through heat exchanger 11 where it was warmed to 297°K in indirect counter-current heat exchange with the incoming feed. A part of this overhead product was then passed through heater 23 where it was further warmed for subsequent use as the regeneration gas for the adsorber. After passing through the adsorber it was recombined with the remainder of the overhead product and the combined stream was then passed to compressor 25 where it was compressed for subsequent use as a fuel gas for combustion in prime movers 4, 21 and 26 driving compressors 3, 19 and 25 respectively. The fuel value of this second product was 222 BTU/cu. ft.

The mole ratio of bottoms product recovered in line 18 to overhead product recovered in line 22 was 64.9 to 35.1.

I claim

1. A process of upgrading a methane gas stream contaminated with a minor but significant quantity of air by fractionation at sub-ambient temperatures and superatmospheric pressures, said process comprising the steps of compressing said air-contaminated methane gas stream to elevated pressure, cooling the compressed gas to condense said gas, expanding the condensate to fractionation pressure and thereafter fractionating said expanded condensate to yield a liquid first product stream having a methane content higher than that of the initial composition and a calorific value commensurate with that of natural gas, and a gaseous second product stream having a methane content below that of the initial composition but above the highest limit of the flammability range of methane-air mixtures under the conditions of temperature and pressure prevailing in said fractionation, said elevated pressure being sufficiently high for substantially the whole of the refrigeration requirements of said cooling step to be provided from said subsequent expansion to fractionation pressure, and said cooling of the compressed gas being effected by indirect countercurrent heat exchange with first product and with evaporating second product.

2. A process as claimed in claim 1 in which at least a part of the energy requirements of the process are provided by combustion of a fuel gas provided by the second product of the fractionation.

3. A process as claimed in claim 1 in which said air-contaminated methane gas stream is compressed in compressor means powered at least in part by prime mover means driven by combustion of a fuel gas provided by said second product stream.

4. A process as claimed in claim 1 in which at least one of said product streams after recovery from said fractionation is compressed to a pressure above said fractionation pressure, and the compression of the air-contaminated gas stream and of said at least one of said product streams is effected by compressor means powered at least in part by prime mover means driven by combustion of a fuel gas provided by said second product stream.

5. A process as claimed in claim 1 in which the air-contaminated methane gas stream contains at least one contaminant which would freeze under the fractionation conditions, and in which prior to condensation said contaminant is removed from said stream by adsorbing said contaminant on an adsorbent therefor, and said adsorbent is thereafter regenerated by the passage therethrough of a regeneration gas provided by one of said product streams.

6. A process as claimed in claim 5 in which before passing it through the adsorbent the regeneration has is directly or indirectly heated by combustion of a fuel gas provided by said second product stream.

7. A process as claimed in claim 5 in which said product stream is compressed after recovery from the fractionation and the regeneration gas is provided from the said compressed product stream.

8. A process as claimed in claim 5 in which said regeneration gas comprises a portion of said one product stream, and after passage through said adsorbent, said regeneration gas is recombined with the remainder of said one product stream for subsequent use as a fuel gas.

9. A process as claimed in claim 7 in which said regeneration gas comprises a portion of said compressed product stream and after passage through said adsorbent said regeneration gas is recombined with the remainder of said compressed product stream for subsequent use as a fuel gas.

10. Apparatus for upgrading an air-contaminated methane composition, said apparatus comprising in combination:
 a. first, second and third compression means each having a gas inlet and a gas outlet,
 b. gas-fuelled prime mover means for driving said first, second and third compression means,
 c. indirect countercurrent heat exchange means,
 d. expansion valve means,
 e. a fractionating column having an inlet, a liquid outlet below said inlet and a gas outlet above said inlet,
 f. a pump having an inlet and outlet,
 g. means for feeding said composition to the inlet of said first compression means,
 h. means for passing compressed composition from the outlet of said first compression means through said indirect countercurrent heat exchange means and then through said expansion valve means where it is expanded to a lower pressure and thence to the inlet of said fractionating column,
 i. means for separating a liquid product from the liquid outlet of said fractionating column into first and second portions, and means for recycling said first portion of said product through said heat exchange means in indirect countercurrent heat exchange with said compressed composition and back to the fractionating column,
 j. means for passing said second portion of the liquid product to the inlet of said pump,
 k. means for passing the liquid product from the outlet of said pump through said heat exchange means in indirect countercurrent heat exchange with said compressed composition and thence to the inlet of said second compression means,
 l. means for recovering a compressed fuel gas from the outlet of said second compression means, m) means for recoverng a gaseous product from the gas outlet of said fractionating column passing it through said m. exchange means in indirect countercurrent heat exchange with said compressed composition and thence to the inlet of said third compression means, and
 n. means for recovering a compressed lean fuel gas from the outlet of said third compression means and for feeding said gas as fuel to said prime mover means, said indirect countercurrent heat exchange means including first and second heat exchangers and in which said first heat exchanger contains first passage means for the passage therethrough of said compressed composition and second and third passage means for the passage therethrough respectively of said gaseous product and said second portion of said liquid product each in countercurrent to said compressed composition, and said second heat exchanger contains first passage means the inlet of which is connected to the outlet of said first passage means of said first heat exchanger for the passage therethrough of said compressed composition after it has traversed said first heat exchanger and second passage means for the passage therethrough of said first portion of said liquid product in countercurrent to said compressed composition.

11. Apparatus as claimed in claim 10 further including: adsorber means comprising at least two beds of adsorbent arranged for cyclic operation such that in each period of the cycle at least one of the beds receives for treatment compressed gas recovered from the outlet of said first compression means, the treated gas being thereafter passed to said heat exchange means, and at least another of the beds is being regenerated for re-use in a subsequent period of the cycle, said regeneration being effected by the passage of regeneration gas therethrough, and means for providing a portion of said gaseous product leaving said heat exchange means to said adsorber means as said regeneration gas.

12. Apparatus as claimed in claim 11 including means for passing the regeneration gas recovered from the adsorber means to the inlet of said third compression means.

13. Apparatus as claimed in claim 10 further including: adsorber means comprising at least two beds of adsorbent arranged for cyclic operation such that in each period of the cycle at least one of the beds receives for treatment compressed gas recovered from the outlet of said first compression means, the treated gas being thereafter passed to said heat exchange means, and at least another of the beds is being regenerated for re-use in a subsequent period of the cycle, said regeneration being effected by the passage of regeneration gas therethrough, and means for providing a part of said compressed lean fuel gas to said adsorber means as regeneration gas.

14. Apparatus as claimed in claim 13 including means for recombining the regeneration gas recovered from said adsorber means with the remainder of the compressed lean fuel gas.

15. Apparatus as claimed in claim 10 in which said first compression means comprises compression means operable with an inlet pressure below atmospheric pressure.

16. Apparatus as claimed in claim 11 further including means for heating the regenerating gas, prior to its passage through said adsorber means, by means of combustion of said compressed lean fuel gas.

17. Apparatus as claimed in claim 13 further including means for heating the regenerating gas, prior to its passage through said adsorber means, by means of combustion of said compressed lean fuel gas.

* * * * *